United States Patent
Mangesius (10) Patent No.: US 11,295,837 B2
(45) Date of Patent: Apr. 5, 2022

(54) DYNAMIC CREATION OF OVERVIEW MESSAGES IN THE HEALTHCARE SECTOR

(71) Applicant: Siemens Healthcare GmbH, Erlangen (DE)

(72) Inventor: Patrick Mangesius, Innsbruck (AT)

(73) Assignee: SIEMENS HEALTHCARE GMBH, Erlangen (DE)

( * ) Notice: Subject to any disclaimer, the term of this patent is extended or adjusted under 35 U.S.C. 154(b) by 335 days.

(21) Appl. No.: 15/968,798

(22) Filed: May 2, 2018

(65) Prior Publication Data

US 2018/0330803 A1    Nov. 15, 2018

(30) Foreign Application Priority Data

May 11, 2017   (EP) .................................... 17170584

(51) Int. Cl.
| | |
|---|---|
| G16H 10/60 | (2018.01) |
| G06F 16/25 | (2019.01) |
| G16H 15/00 | (2018.01) |
| G06F 21/62 | (2013.01) |
| G06F 16/2455 | (2019.01) |
| G16H 20/00 | (2018.01) |

(52) U.S. Cl.
CPC ......... *G16H 10/60* (2018.01); *G06F 16/2455* (2019.01); *G06F 16/252* (2019.01); *G06F 21/6218* (2013.01); *G06F 21/6245* (2013.01); *G16H 15/00* (2018.01); *G16H 20/00* (2018.01)

(58) Field of Classification Search
None
See application file for complete search history.

(56) References Cited

U.S. PATENT DOCUMENTS

| | | | | |
|---|---|---|---|---|
| 2003/0220817 | A1* | 11/2003 | Larsen | G16H 40/67 705/2 |
| 2006/0080140 | A1* | 4/2006 | Buttner | G06Q 10/10 705/2 |
| 2008/0046292 | A1* | 2/2008 | Myers | G06F 16/283 705/3 |
| 2008/0306872 | A1* | 12/2008 | Felsher | G06Q 20/367 705/51 |
| 2009/0192941 | A1* | 7/2009 | Fournier | G06F 21/6254 705/51 |

(Continued)

FOREIGN PATENT DOCUMENTS

KR         20090001730 A  *  1/2009

OTHER PUBLICATIONS

D Hanauer, EMERSE Electronic Medical Record Search Engine Technical Manual, Feb. 8, 2016, Project EMERSE (Year: 2016).*

(Continued)

*Primary Examiner* — Aryan E Weisenfeld
*Assistant Examiner* — Karen A Hranek
(74) *Attorney, Agent, or Firm* — Harness, Dickey & Pierce, P.L.C.

(57) ABSTRACT

A method, a system and different nodes are for the provision of an overview message for a patient. The overview message summarizes all relevant data records stored on the previous treatment of the patient and contains references for accessing the respective documents containing the components of the overview message, and for which it has been possible to validate access authorizations. As such, only permissible access to sensitive databases is provided.

17 Claims, 3 Drawing Sheets

(56) References Cited

U.S. PATENT DOCUMENTS

| | | | | |
|---|---|---|---|---|
| 2010/0082369 A1* | 4/2010 | Prenelus | ............... | G16H 10/60 |
| | | | | 705/3 |
| 2010/0268553 A1* | 10/2010 | Bessette | ............... | G06Q 99/00 |
| | | | | 705/3 |
| 2011/0295873 A1* | 12/2011 | Potter | ................... | G06F 16/93 |
| | | | | 707/769 |
| 2012/0253842 A1 | 10/2012 | Curran | | |
| 2012/0323601 A1* | 12/2012 | Huang | .................. | G06Q 50/24 |
| | | | | 705/3 |
| 2013/0006665 A1* | 1/2013 | Fernandez | ............ | G16H 50/70 |
| | | | | 705/3 |
| 2014/0324479 A1* | 10/2014 | Dufel | ..................... | G16H 10/60 |
| | | | | 705/3 |
| 2014/0350961 A1* | 11/2014 | Csurka | .................. | G16H 10/60 |
| | | | | 705/3 |
| 2014/0379378 A1 | 12/2014 | Cohen-Solal | | |
| 2015/0294088 A1 | 10/2015 | Walker | | |
| 2016/0277374 A1* | 9/2016 | Reid | .................... | H04L 63/101 |
| 2016/0357909 A1* | 12/2016 | Northam | ................ | G06F 19/00 |

OTHER PUBLICATIONS

Integrating the Healthcare Enterprise, IHE IT Infrastructure (ITI) Technical Framework, Sep. 18, 2015, vol. 1 (Year: 2015).*

Mangesius, Patrick et al.: "Patient Summaries in Context of Large Scale EHR Networks with Fine Granular Access Control Restrictions"; in: PHEALTH 2017; pp. 91-96; XP009195290; ISBN: 978-1-61499-760-3; 2017.

Extended European Search Report #17170584.1 dated Sep. 7, 2017.

* cited by examiner

DYNAMIC CREATION OF OVERVIEW MESSAGES IN THE HEALTHCARE SECTOR

PRIORITY STATEMENT

The present application hereby claims priority under 35 U.S.C. § 119 to European patent application number EP17170584.1 filed May 11, 2017, the entire contents of which are hereby incorporated herein by reference.

FIELD

At least one embodiment of the present invention generally relates to methods and/or a system for creating an overview message for a patient based on a standardized platform.

BACKGROUND

Medical or health-related data on a patient is generated in different enterprises, such as hospital and institutes. Hence, it is available in distributed form (locally). The respective enterprises are typically connected by a network. The data is increasingly acquired digitally or at least stored in digital form.

To improve the quality of treatment for the patient and to increase the safety of the treatment, it is desirable for the exchange of data between the different distributed enterprises to be improved. This also helps to avoid unnecessary repeat examinations and to reduce costs in the health sector overall.

In many countries, central storage of medical data is not possible due to data protection regulations. This means that medical data, such as, for example, medical history, previous findings or reports, generated image data etc. are not allowed, at least not in insecure form, to leave the sphere of the respective enterprise in which they were acquired; hence the data remains local and is therefore provided in distributed and decentralized form.

A further problem in the prior art resides in the fact that the amount of data (stored medical data) is increasing. Hence, the selection of relevant data for the respective application is a challenging task. Even if the data were not contained in decentralized repositories but were centralized, the extraction of relevant information from these very extensive data volumes would still be a computing-intensive and resource-intensive task since it is necessary to search a large number of different files occupying a large amount of memory space. However, the local enterprises are not always equipped with the necessary infrastructure (information technology).

Another complicating factor to take into account is the fact that the requirements for the selection of data can be very different. On the one hand, it is necessary to take account of different authorizations for subscribers (for example in the role of doctor, patient, staff etc.), which could also change over time, and on the other, applications and medical questions vary. For example, it makes a difference whether the data is to be acquired for a medical study or for a specific diagnosis for a patient with the latter generally requiring more detailed data.

Hence, it is desirable for health data also to be made available beyond the boundaries of the respective enterprise and at the same time to comply with the above-mentioned restrictions and specifications.

In the prior art, the exchange of electronic health data in EHR systems (EHR—Electronic Health Record) between distributed institutions is typically based on standards. IHE (IHE—Integrating the Healthcare Enterprise) is for example an international initiative by users and producers with the aim of standardizing and harmonizing data exchange between IT systems in the healthcare sector. XDS (Cross-Enterprise Document Sharing) is an example of a system for exchanging documents between enterprises. Three different components are provided in IHE XDS based environments:
1. an XDS-Source that generates data (for example an imaging system or scanner),
2. an XDS repository used for persistent local storage of the acquired data and registration thereof in the repository and
3. a central registry.

The registry is responsible for the storage of metadata on the generated data or documents so that the relevant documents for the treatment of a patient are easy to find, select and retrieve independently of the repository, i.e. independently of the storage location (in the clinical enterprise) in which they are actually stored. To this end, the metadata contains an indicator (pointer, link, reference) to the storage location of the document in the repository in the respective local enterprise (for example in an information technology unit in the hospital etc.). Several local repositories in one or different enterprise(s) can be connected to one registry. An important aspect in this standard is the fact that the registry does not have access to the documents stored in the repository; it only has pointers indicating the storage location. This precaution is to ensure compliance with the security regulations, namely to ensure that safety-critical medical data does not leave the respective enterprise. A client or data sink can access the documents in the repository if access authorization has been assigned.

As mentioned above, the high volume of data means the provision of relevant data is a challenging task. To this end, it is possible to use an overview document or a patient-specific summary file. The HL7 (Health Level 7) Standard already defines a so-called C-CDA document for the exchange of data between organizations in the healthcare sector for this purpose. "CDA" stands for "Clinical Document Architecture" and the prefix "C-" for "Consolidated". CDA is a XML-based markup standard for all clinical documents in the health sector. Hence, this standard already specifies an overview document. However, in the prior art, the generation of an overview document is very complex, since, in order to extract a component of the overview document, it is in each case necessary to open and search through the corresponding basic document containing said component.

In view of the technical requirements described in the introduction (security, data protection, etc.), in IHE XDS based systems, it has been necessary to open each individual document in order to extract data relevant for an overview display therefrom. If, for example, an overview file for a special application is to include information on the weight and age of the patient, with the systems used to date, it is necessary to open a first file in which information on weight is stored and retrieve this data and open a second file in which information on age is held. It is evident to a person skilled in the art that, even if it is automated, this procedure is very computing-intensive and time-intensive and hence very resource-intensive.

SUMMARY

At least one embodiment of the present invention discloses a way to improve data exchange in the health sector while complying with the above-described restrictions and requirements. In particular, this should make it possible, on a client's request, to generate an overview document from a plurality of decentralized data sources in a dynamic manner and at the same to comply with the access authorizations of the respective clients with variable authorization rules.

Advantageous embodiments are the subject matter of the claims, the description and the drawings.

According to a first embodiment, a method is for operating an extraction service for generating an (electronic) extraction message for a patient based on a standardized platform comprising the following method steps:
  reading-in a data record from a local data source;
  selecting parameters of the read-in data record for generating an extraction message;
  sending the extraction message to a central broker service.

According to a second embodiment, a method is disclosed for operating a central broker service for handling a request from a client for an overview message for a patient based on a standardized platform, comprising:
  receiving the request from the client;
  resolving the received request and determining a client identifier and ascertaining parameters of the requested overview message;
  accessing a database in order to aggregate extraction messages that correspond to the ascertained parameters;
  accessing a central registry in order, on the basis of the client identifier determined, to check an existing authorization for the client to access the respective document containing the respective parameter for all aggregated extraction messages and, in the case of affirmation, (i.e. the authorization exists):
  insertion of the respective parameter in the overview message and iterative
  creation of the overview message.

In another embodiment, the invention relates to an extraction node for generating an extraction message for a patient based on a standardized platform comprising:
  an extraction-input interface provided to read in a data record from a local data source;
  a computing unit provided to select parameters of the read-in data record in order to generate an extraction message;
  an extraction-output interface provided to send the extraction message to a central broker service.

In another embodiment, the invention relates to a central broker node used to execute a broker service for handling a request from a client for an overview message for a patient based on a standardized platform comprising:
  a broker-input interface used to receive the request from the client;
  a broker-extraction interface provided to read in an extraction message;
  a processing unit provided to resolve the received request and to determine a client identifier and to ascertain the parameters of the requested overview message;
  and wherein the processing unit is furthermore provided to access a database in order to aggregate the extraction messages that correspond to the ascertained parameters;
  and wherein the processing unit is furthermore provided to access a central registry in order, on the basis of the client identifier determined, to check an existing authorization for the client to access the respective document containing the respective parameter of all aggregated extraction messages and
  wherein, if authorization exists, the processing unit is provided to insert the respective parameter in the overview message and to create the overview message.

In another embodiment, the invention relates to a system for generating an overview message for a patient based on a standardized platform and for operating a central broker service and an extraction service, with:
  an extraction-input interface provided to read in a data record from a local data source;
  a computing unit provided to select parameters of the read-in data record in order to generate an extraction message;
  an extraction-output interface provided to send the extraction message to a central broker service;
  a local repository provided for local storage of the generated data records and for sending metadata for the generated data records with a link to the data records to a central registry;
  a broker-input interface used to receive the request from the client;
  a broker-extraction interface, which is in data exchange with the extraction-output interface and provided to read in an extraction message;
  a processing unit provided to resolve the received request and to determine a client identifier and to ascertain the parameters of the requested overview message;
  and wherein the processing unit is furthermore provided to access a database in order to aggregate the extraction messages that correspond to the ascertained parameters;
  and wherein the processing unit is furthermore provided to access the central registry in order, on the basis of the client identifier determined, to check an existing authorization for the client to access the respective document containing the respective parameter of all aggregated extraction messages and
  wherein, if authorization exists, the processing unit is provided to insert the respective parameter in the overview message and to create the overview message.

According to a further embodiment, the present invention relates to a method corresponding to the above-described system. The method is distributed, both locally on the extraction node and centrally on the broker node. Hence, the method is used to operate an extraction service on an extraction node and a broker service on a broker node for generating an (electronic) extraction message for a patient based on a standardized platform comprising:
1. reading-in a data record from a local data source;
2. selecting parameters of the read-in data record for generating an extraction message;
3. sending the extraction message to a central broker service;
4. receiving the request from the client;
5. resolving the received request and determining a client identifier and ascertaining parameters of the requested overview message;
6. accessing a database in order to aggregate the extraction messages that correspond to the ascertained parameters;
7. accessing a central registry in order, on the basis of the client identifier determined, to check an existing authorization for the client to access the respective document containing the respective parameter of all aggregated extraction messages and, in the case of affirmation, (i.e. if authorization exists):
8. insertion of the respective parameter in the overview message and iterative
9. creation of the overview message.

A further embodiment provides a computer program with computer program code for carrying out all the method steps of embodiments of the above-described methods (on the different nodes) when the computer program is executed on a computer or on the respective node. Herein, it is also possible for the computer program to be stored on a computer-readable medium.

A further embodiment provides a non-transitory computer program product, including a computer program directly loadable into a memory of a computer, the computer program including computer program code for executing an embodiment of the method when the computer program code is executed on a computer.

A further embodiment provides a non-transitory computer readable medium storing computer program code for executing an embodiment of the method when the computer program code is executed on a computer.

BRIEF DESCRIPTION OF THE DRAWINGS

The more detailed description of the figures given below discusses example embodiments, which are not to be understood as restrictive, with their features and further advantages with reference to the drawings, which shows.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The health sector generates an enormous amount of data that has to be managed. For medical questions, it is important to have targeted access to relevant data that can be calculated from distributed data sources. One embodiment of the invention relates to the generation of such relevant data in form of an overview message or in form of a patient summary file.

The following determines the terminology used for the purposes of embodiments of this application.

The registry is a digital memory that is held centrally. It can be addressed as a cloud memory via corresponding network accesses. It is preferably an XDS registry. The registry is used as a metadata document index, i.e. as a metadata index for the acquired data records.

The repository is a digital memory, for example in the form of a hard disk or a RAID system that is held locally. It is used for local storage of the acquired data records or documents. It is preferably embodied as an XDS repository.

The term "data record" can also be understood in the sense of "document". First, data records are acquired on a data source (technical facility in the healthcare sector), such as, for example, an imaging device or a scanner or another type of medical apparatus. These data records are stored in a document and can be further processed. The document can have a specific structure that facilitates automatic processing. The structure can be based on a standard. The structure is preferably based on an IHE XDS-Standard and is a CDA-formatted document (CDA: Clinical Document Architecture). Other embodiments of the invention use a different format.

The broker service is a service that is executed on a computer-based node with a processing unit. To this end, a broker node is provided to execute the broker service. The broker service can be implemented in software. The broker service is provided as a central service. The broker service is preferably embodied to be integrated in an IHE XDS platform.

The extraction service is a service that is executed on a computer-based node with a computing unit. To this end, an extraction node is provided to execute the extraction. The extraction service can be implemented in software. The extraction service is provided as a local service (for example in a hospital or assigned to a client). The extraction service is preferably embodied to be integrated in an IHE XDS platform.

A client is an electronic instance, such as, for example, a computer-based unit, such as a computer, a mobile device, a tablet, a smartphone or a workstation. The client can be operated by different users in different roles (for example physicians, nursing and care staff). Different access rights to the data can be assigned depending on the role. These rights can be implemented in an access rights management system. The client can function as a sender and a receiver of data records. The client can be used to ascertain the overview message or to generate data records (for example a doctor's report).

The overview message is an electronic data record intended to serve as a summary of the previous treatment of the patient or—in complex cases—sections thereof. A structured document (for example CDA document) transmitted from a data source (for example a medical device) can send one or more observation messages or extraction messages to the service (in particular first to the local extraction service and then to the central broker service). If, for example, a document includes information on allergies and weight, it is also possible to generate therefrom a first message with <allergies> and a second message with <weight>, depending upon the selected implementation. The overview message is used for the overview-type representation of evaluated patient-specific data records, data and/or parameter values or more complex compilations of data in the form of reports, findings or other medical results that are aggregated and summarized in the overview message.

In addition, to the medical or health-related data, the overview message contains a reference that uniquely identifies the patient (patient identifier) and a reference that uniquely identifies the respective document containing the component or parameter of the overview message (document identifier). The individual components of the overview message are usually distributed on different systems and in different formats. In addition, they are not allowed to leave the respective network (unprotected). The components to be contained in the overview message can preferably be configured in a preparation phase. Thus, in one embodiment of the invention, it is, for example, possible for the patient's weight, age, existing allergies and the current medication to be determined as components of the overview message. The data is preferably structured such that it can be processed efficiently and read-in. They can, for example, be formatted as a string composed of the respective components.

According to one example embodiment of the invention, the overview message has a dual functionality. On the one hand, it contains the respective desired preconfigurable components (for example age, weight etc.) and, on the other, it contains a reference (link) to the respective document that contains the respective component (i.e. overall, a set of references to a set of documents stored in distributed fashion). When required, a client to whom the overview message is supplied by way of the method or system suggested here can then access further, more detailed information via the link. This can, so-to-speak, be performed optionally and in a second step. However, the overview message enables the client first to inspect a patient-specific summary of parameter values or other data in a first step without having to open the individual documents containing the parameters. Hence, this can advantageously greatly reduce the access times and the time required to search for medical details in extensive document collections.

The extraction message is an electronic data record that is extracted from the acquired medical data in the data source. The extraction is performed by a specific service, namely the extraction service. The extraction service can also be configured in the preparation phase with respect to which elements it is to extract from the acquired data record. In the case of simple numerical types (age, weight etc.), the extraction message includes the type (for example weight) and the respective value (for example 75 kg). In the case of complex types (for example MRI images), only one kind of type specification can be extracted (specification: image or MRI image or an anatomical region represented in the image).

The respective nodes (for example extraction node, broker node) are computer-based hardware units. A node can be embodied as a network node. This can, in particular be a device that takes over switching functions or also an apparatus working on the network periphery as an interworking unit. A node can be a controller, node computer, terminal, printer, disk drive, minicomputer, gateway or another facility. A node can multiply, divide and statistically assign data channels and switch data transmission channels by way of dynamic assignment.

The interfaces described are components of the technical system that are used for communication. The interface can be embodied as a network interface (for example a WLAN or another radio interface). It is also possible for several interfaces to be provided for each network segment or communication device, such as, for example, when using a bridge with at least two network interfaces (wherein the bridge ensures that signals, protocols and/or transmission systems are converted if the communicating systems do not have a common interface) or when using hubs and switches or routers. At another ISO/OSI level, the interface can also be embodied as a software interface and the respective applications or operating system program connected by a data link. Hence, the interfaces can be software data interfaces providing logical connections in a software system. These facilitate and regulate the exchange of commands and/or data between different processes and components. The interface can be provided for inter-process communication and/or as an interface for program components. In particular, the wireless interfaces of known network protocols, such as TCP, HTTP etc., are understood to be interfaces.

The processing unit and the computing unit are computer-based instances that are used to execute computer programs. This can in particular entail a processor, a microcontroller and/or a microprocessor. The processing and computing unit can be embodied as a central processing unit (CPU) and be used to process program commands. It can include a computing unit and a control unit and communication interfaces.

According to a first embodiment, a method is for operating an extraction service for generating an (electronic) extraction message for a patient based on a standardized platform comprising the following method steps:

reading-in a data record from a local data source;
selecting parameters of the read-in data record for generating an extraction message;
sending the extraction message to a central broker service.

It is provided according to the IHE XDS-Standard that the read-in data record is sent to a local repository for storage. The repository is embodied to send metadata from the (received from the data source) data record to a central registry for purposes of registration. Hence, the registry only contains metadata for the data acquired at the data source. The actual (binary) data is only stored locally in the repository.

According to one example embodiment of the invention, the operational sequence is based on this standardized procedure. Therefore, it can be considered to be an important advantage that the standard operational sequence does not have to be changed or influenced in order to achieve the advantages of the invention. It is not necessary for the hospitals or the connected clients to purchase new hardware (or software). All that is required is the provision of two services (a local extraction service and a central broker service). These can advantageously be integrated and implemented on existing nodes. In principle, the concept presented here and the invention can also be used with other standards and also with proprietary standards and also with non-standard-compliant systems; it does not need to interact exclusively with XDS.

In one advantageous embodiment of the method it is possible to preconfigure (in a configuration phase of the method) those parameters which are to be extracted from the read-in data record. This means that the method can be divided into an execution phase and an upstream configuration phase and that the parameters that are to be extracted on principle can be set in the configuration phase. These parameters are identified as extractable.

According to a further advantageous embodiment of the method, the extraction message includes at least the following elements:
 a patient identifier that uniquely identifies the respective patient;
 a document identifier that uniquely references a storage location for metadata for the read-in data record from which (data record) the data was extracted;
 a configurable selection of extracted parameters, in particular specifying a parameter type (for example weight, age, allergies etc.) and the value thereof (for example 67 kg, 35, hay fever). Preferably, herein a code is used that uniquely identifies a parameter type. Hence, in one example embodiment of the invention, a parameter is identified by the specification of a parameter type and the corresponding value.

It should be noted that the term "parameter" is used in different contexts or instances in the application. For example, there are parameters that are contained in the requested overview message, in the created overview message, in the extraction message and in aggregated extraction messages. Hence, the parameter (with the specification of parameter type and parameter value) references the respective assigned data records and serves as an index from a technical viewpoint. The index enables the storage position of the respective requested data record within the storage medium to be identified quickly so that it is only necessary to search in a subset of stored data. This has the technical advantage that a rapid search in large volumes of data can be performed efficiently while simultaneously complying with security regulations and access regulations.

If, for example, the requested overview message is to include the parameter "blood group", the parameter "blood group" is first determined from the overview message in order then to access the database in order to assemble and combine those extraction messages that include the parameter "blood group". Then, following access to the central registry, the access right of the requesting client to the "blood group" data records is determined for the aggregated extraction messages and, only if an authorization can be validated, is the respective parameter included in the overview message to be created. If, for example, the database contains two different data records including the parameter "blood group", namely a first data record including a diagnosis (for example in form of a diagnosis "AIDS" with reference to the blood group in a doctor's report) and a second data record including a data extract from an immunization card, it is, for example, possible for the client to have access authorization for the second data record but not for the first data record. In this case, only the second data record will be referenced in the overview message to be created since authorization only exists for this.

According to a second embodiment, a method is disclosed for operating a central broker service for handling a request from a client for an overview message for a patient based on a standardized platform, comprising:
 receiving the request from the client;
 resolving the received request and determining a client identifier and ascertaining parameters of the requested overview message;
 accessing a database in order to aggregate extraction messages that correspond to the ascertained parameters;
 accessing a central registry in order, on the basis of the client identifier determined, to check an existing authorization for the client to access the respective document containing the respective parameter for all aggregated extraction messages and, in the case of affirmation, (i.e. the authorization exists):
 insertion of the respective parameter in the overview message and iterative
 creation of the overview message.

In one example embodiment of the invention, the overview message is generated dynamically and only when required upon request of the client and in particular during access (to the database). This advantageously enables compliance with the safety regulations and ensures that the data to be protected is exclusively stored persistently locally or on site (of the data acquisition).

According to a further embodiment of the invention, the overview message is supplied as a fully structured document and is in particular formatted in accordance with a CDA standard. This facilitates the further processing of the data and integration of the overview message in other standardized systems.

According to a further example embodiment of the invention, authorization rules are held in the central registry and these rules can also be varied during the execution of the method. The authorization rules are used to establish the client's access rights. Advantageously, separate storage of the authorization rules enables dynamic adaptation to the application in question.

According to a further example embodiment of the invention, during the generation of the overview message, the access authorization of the requesting client and/or contextual parameters of the request are taken into account. Different access rights to the respective data records apply depending upon the role (for example, the position of the user with different dedicated access authorization in each case) and context (for example purpose and background or significance of the request, for example for a diagnosis or for a study) of a request. Advantageously, the authorization rules can also be changed during operation without it being necessary to restart the method. The definition of a user role (or role for short) is known practice in information technology.

Herein, it is possible to summarize a set of individual rights to access safety-critical data and/or software. User roles are used so that it is not necessary to establish the individual rights to the aforementioned regions individually for each user: instead of directly assigning the same individual rights to a large number of users, a user role is defined that contains the rights to be assigned. Users are then assigned the corresponding respective role. This facilitates the rights management in the software system, since in particular in the case of changes to the rights structure, it is only necessary to change the rights of the user role. The rights management can be implemented in an access control system. Preferably, the client's user interface is adapted to the client's user role, i.e., depending the authorizations held, the client is able to generate more extensive requests or simple requests only. The user role with the access authorizations can be provided in a mobile data carrier that can be read via a wireless interface (for example in form of a chip card or a RFID tag).

According to a further example embodiment of the invention, to generate the overview message, the requested parameters thereof are filtered in accordance with configurable filter criteria.

According to a further example embodiment of the invention, the overview message includes a link to the respective document containing the requested parameter(s). As a rule, the overview message contains a set of parameters, and hence a set of links, which refer to the respective documents or the storage location thereof. As already described above, in an upstream step, the respective access rights for the client to the documents are checked and stored centrally (preferably in the registry). In one example embodiment of the invention, this can be performed by way of an authorization service (access control system). If, during operation, an access right could not be validated (i.e. no access is allowed), the parameter is automatically removed from overview message and, correspondingly, also does not contain a link to the document.

According to a further example embodiment of the invention, the overview message is not stored in the registry. It is preferably not stored on a node but provided to the client on request. This enables increased security and the avoidance of unauthorized use of the data.

According to a further example embodiment of the invention, all calculations for the generation of the overview message are executed in full by the central broker service. This has the important advantage that the entire computing load and resource consumption can be so-to-speak outsourced to the server or into the cloud. Optionally, it also possible to access an access control or authorization system.

According to a further example embodiment of the invention, the standardized platform is an IHE XDS platform.

In another embodiment, the invention relates to an extraction node for generating an extraction message for a patient based on a standardized platform comprising:
an extraction-input interface provided to read in a data record from a local data source;
a computing unit provided to select parameters of the read-in data record in order to generate an extraction message;
an extraction-output interface provided to send the extraction message to a central broker service.

In another embodiment, the invention relates to a central broker node used to execute a broker service for handling a request from a client for an overview message for a patient based on a standardized platform comprising:
a broker-input interface used to receive the request from the client;
a broker-extraction interface provided to read in an extraction message;
a processing unit provided to resolve the received request and to determine a client identifier and to ascertain the parameters of the requested overview message;
and wherein the processing unit is furthermore provided to access a database in order to aggregate the extraction messages that correspond to the ascertained parameters;
and wherein the processing unit is furthermore provided to access a central registry in order, on the basis of the client identifier determined, to check an existing authorization for the client to access the respective document containing the respective parameter of all aggregated extraction messages and
wherein, if authorization exists, the processing unit is provided to insert the respective parameter in the overview message and to create the overview message.

In another embodiment, the invention relates to a system for generating an overview message for a patient based on a standardized platform and for operating a central broker service and an extraction service, with:
an extraction-input interface provided to read in a data record from a local data source;
a computing unit provided to select parameters of the read-in data record in order to generate an extraction message;
an extraction-output interface provided to send the extraction message to a central broker service;
a local repository provided for local storage of the generated data records and for sending metadata for the generated data records with a link to the data records to a central registry;
a broker-input interface used to receive the request from the client;
a broker-extraction interface, which is in data exchange with the extraction-output interface and provided to read in an extraction message;
a processing unit provided to resolve the received request and to determine a client identifier and to ascertain the parameters of the requested overview message;
and wherein the processing unit is furthermore provided to access a database in order to aggregate the extraction messages that correspond to the ascertained parameters;
and wherein the processing unit is furthermore provided to access the central registry in order, on the basis of the client identifier determined, to check an existing authorization for the client to access the respective document containing the respective parameter of all aggregated extraction messages and
wherein, if authorization exists, the processing unit is provided to insert the respective parameter in the overview message and to create the overview message.

According to a further embodiment, the present invention relates to a method corresponding to the above-described system. The method is distributed, both locally on the extraction node and centrally on the broker node. Hence, the method is used to operate an extraction service on an extraction node and a broker service on a broker node for generating an (electronic) extraction message for a patient based on a standardized platform comprising:

1. reading-in a data record from a local data source;
2. selecting parameters of the read-in data record for generating an extraction message;
3. sending the extraction message to a central broker service;
4. receiving the request from the client;
5. resolving the received request and determining a client identifier and ascertaining parameters of the requested overview message;
6. accessing a database in order to aggregate the extraction messages that correspond to the ascertained parameters;
7. accessing a central registry in order, on the basis of the client identifier determined, to check an existing authorization for the client to access the respective document containing the respective parameter of all aggregated extraction messages and, in the case of affirmation, (i.e. if authorization exists):
8. insertion of the respective parameter in the overview message and iterative
9. creation of the overview message.

Herein, steps 1 to 3 are performed on the extraction node and the remaining steps (4 to 9) on the broker node or centrally on distributed cloud-based network nodes.

An important advantage of the above-described example embodiment can be seen in the fact that the computing load for the provision of the overview message as a patient summary in the network can be shifted to a server or into the cloud and does not occur locally on the requesting client. Furthermore, it is seamlessly possible to refer to existing standards and comply with security regulations for protected, sensitive data in the healthcare sector (PHI data, protected health data). These specify inter alia that the local medical data acquired in an enterprise (hospital) for a patient is only stored in this enterprise and not made available externally. Thus, it is not possible to use known methods from the prior art, which work, for example with web crawlers.

The above references a method, specific nodes and a system. Features, advantages or alternative embodiments mentioned herein can also be transferred to the other claimed subject matter and vice versa. In other words, the material claims (directed for example at a system, a node or a computer program product) can also be directed with the features which are described or claimed in connection with the method. Herein, the corresponding functional features of the method are formed by corresponding material modules, in particular hardware modules or microprocessor modules, of the system or the product and vice versa.

A further embodiment provides a computer program with computer program code for carrying out all the method steps of embodiments of the above-described methods (on the different nodes) when the computer program is executed on a computer or on the respective node. Herein, it is also possible for the computer program to be stored on a computer-readable medium.

A further embodiment provides a computer program product, which can be loaded directly into the memory of a digital computer and includes computer program code to execute embodiments of the above-described method when the computer program product is executed on a computer.

Embodiments of the invention relates to the automatic generation of an overview document, which is referred to in the following as an overview message and given the reference uen in the figures.

The overview message uen is intended to provide a user (physician or the actual patient or other participants) working on a computer node embodied as a client CL with an overview of existing health data for the patient. The compilation of the overview message uen should be configurable. In particular—depending upon the application—it should be possible to determine which parameters the overview message uen should include. In a first example, the overview message uen for a patient "Huber" is to include the weight and the blood group, while, in a second example, it is to include allergies, findings of operations performed and reports for the same patient.

According to one example embodiment of the invention, account is also taken of the role of the requesting client CL and the situational context of the request an (request context) in the generation of the overview message uen. This has the following background: medical authorization systems generally include roles, which are assigned to a user/client and linked to rights. For example, a user in the role "physician" is permitted to see radiological findings and discharge notes, while a user in the role "care staff" is only permitted to see discharge notes. In order to enable an automatic check as to whether the respective user has access authorization for the document from which the information or parameters were extracted, the rights and roles of the user are acquired on request. The request context is also acquired. This represents, for example, the purpose for which the overview message uen is to be generated (for example study, diagnosis etc.).

To create the overview message uen, it is necessary for various legal conditions to be observed. For example, it must be ensured that patient-specific data does not leave the sphere of the clinical enterprise in which it was acquired. I.e. it must be stored locally.

In order to be able to observe these legal conditions and further requirements, use is preferably made of a standardized platform for message exchange. In principle, there are several options for this. One preferred standard is an IHE Standard, in particular an IHE XDS platform.

The IHE XDS-Standard has three components:
a local data source XDS-S on which the data is generated, for example an MRI device or another imaging facility or a blood-pressure measuring device etc. The data source XDS-S generates data records ds;
a local memory, which can be embodied as an XDS repository XDS-REP. It is used for persistent storage of the binary data ds and for forwarding metadata to a central registry XDS-REG;
the central registry XDS-REG. This is used to store the metadata for the data records ds acquired at the local data source XDS-S with a pointer to its storage location, i.e. to the local repository XDS-REP. The data records ds are not stored in the central registry XDS-REG, but only registered there.

This standard-compliant architecture is expanded according to the invention by two interacting nodes:
a local extraction node OES and
a central broker node OBS.

The extraction node OES preferably embodied to perform an extraction service. The broker node OBS is preferably embodied to perform a broker service.

The interaction of these components is explained in more detail in the following with reference to FIG. 1.

The extraction service is used to receive the acquired data records ds from which it extracts, in accordance with pre-configurable rules, certain parameters of interest that should on principle be available for overview messages. Hence, the extraction service generates an excerpt from the respective data record ds and structures this excerpt in the form of an extraction message en and sends this to the central broker service. An HL7 FHIR transaction (FHIR: Fast Healthcare Interoperability Resources) can be used for the transfer.

The extraction message en includes at least the following entries:
  a patient identifier; this is a unique identification number that identifies the patient
  a document identifier; this is also a unique identification number that identifies the document or refers to its storage location from which the extracted parameters were acquired
  the respective parameters.

The central broker service is used to receive the extraction message en. Furthermore, it is a receiver node for a request from the client CL. For example, the client CL, in the function of an anesthetist, wishes to obtain an overview for a certain patient Huber for planning the forthcoming anesthesia for a surgical intervention. To this end, the client is interested in special parameters, such as allergies, weight and age of the patient and anesthetic gases used in previous operations. For this, the client creates a configured request an including the parameters allergies, weight, age and anesthetic gases. This request is forwarded via a transaction, preferably a HL7 FHIR transaction, to the central broker service.

On receipt, the central broker service resolves the request an and extracts or determines a client identifier identifying the requesting client CL. Herein, it is possible for both a role of the requesting person (property as a physician, in particular anesthetist) and the context of the request (for forthcoming anesthesia) to be taken into account. To this end, the client identifier includes identifying elements. The central broker service also determines the desired parameters for the requested overview message uen for the respective patient. The request an is usually patient-specific. However, it is also possible for several requests an to be combined to form a more complex query (for example "overview of all patients with operation appointment tomorrow in respect of the parameters allergies, weight, age and anesthetic gases"), which then covers all patients.

The central broker service uses the parameters determined to access a database DB in order to find the entries or the extraction messages that include the desired parameters. Hence, the database access ascertains a set of extraction messages, which—in the above example—contains information on allergies, weight, age and anesthetic gases for the patient Huber.

However, since the requesting client C1 does not always have access authorization for all documents, the central broker has to carry out service further transactions to check the respective authorizations of the client C1 for the documents. To this end, it preferably accesses the central registry XDS-REG. This can take place via an ITI-18 or ITI-61 transaction. In one advantageous alternative embodiment of the invention, the central registry XDS-REG can also be accessed indirectly, by mediation of an authorization system (access control system—ACS).

The central broker service or the authorization system now performs, for the list with the matching extraction messages, repeated checks for each of the extraction messages to identify which parameters it includes and from which document the respective parameter originates in order to ascertain whether the requesting client CL is authorized to access the respective document. The respective parameter is only included in the overview message uen to be generated if authorization could be established. Otherwise, (no authorization), the parameter is not included in the overview message uen.

In multiple iterations, the overview message uen can ultimately so-to-speak be generated on-the-fly and supplies as a structured document to the requesting client CL. Communication between the client CL and the central broker service can take place using an ITI-43 or a HL7 FHIR transaction.

Figure 1:
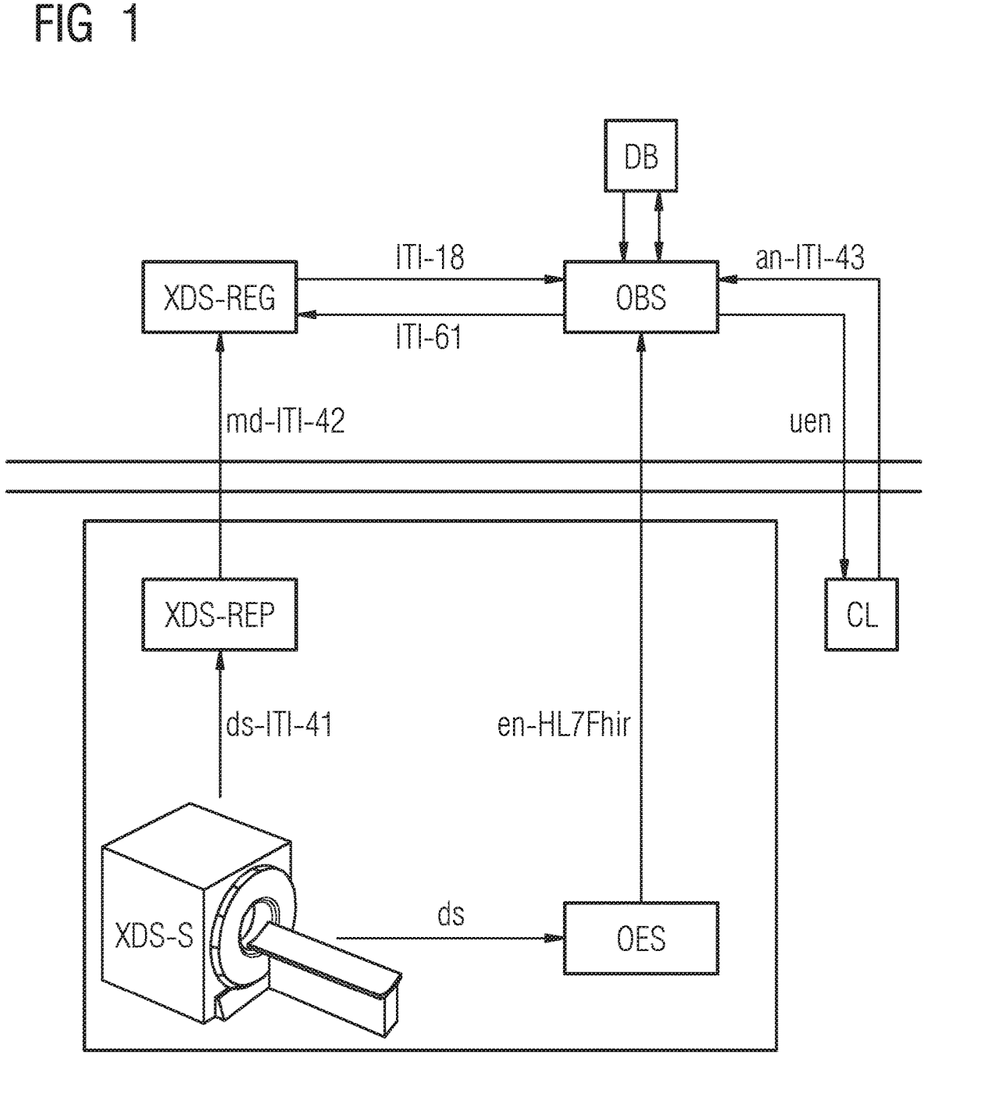
FIG. 1 shows a schematic overview display of a system for the central creation of an overview message according to one example embodiment of the invention.

As shown in FIG. 1, the data source XDS-S, the extraction service and the storage system XDS-REP are positioned locally in a clinical enterprise. The corresponding nodes XDS-S, OES, XDS-REP communicate via standardized protocols, such as, for example, via ITI-41. This is a transaction with a so-called "provide and register document set-b" message as a payload. The payload of the message can contain metadata md for the acquired data record with the access authorizations and further metadata, such as, for example, a time stamp, for the respective data source XDS-S etc.

The metadata md is sent with a link to the storage location of the data ds to a central registry XDS-REG for registration. The registry XDS-REG is provided as a central instance and can so-to-speak be shifted into the cloud. As a central instance, the broker service is also provided on the broker node OBS, which is also in data exchange with the other components via a suitable network connection.

Communication between the local repository XDS-REP and the central registry XDS-REG can, for example, take place via an ITI-42 transaction.

Figure 2:
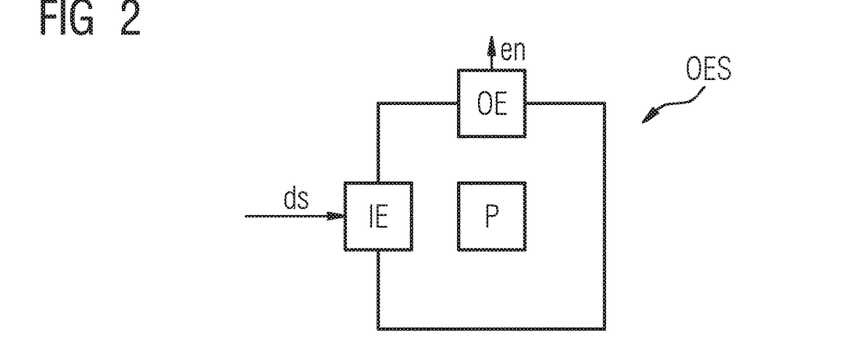
FIG. 2 shows a block diagram of a node that implements a local extraction service according to one example embodiment of the invention.

FIG. 2 is a schematic depiction of the architecture of the extraction node OES on which the extraction service is implemented. It includes an extraction-input interface IE to receive the data records ds acquired at the data source XDS-S and a computing unit P for the extraction of relevant parameters from the data records ds. The computing unit P calculates the extraction message en and sends it via the extraction-output interface OE to the central broker service. The extraction service can optionally comprise further components, such as, for example, a cache or a memory for (interim) storage of the extraction message en generated.

Figure 3:
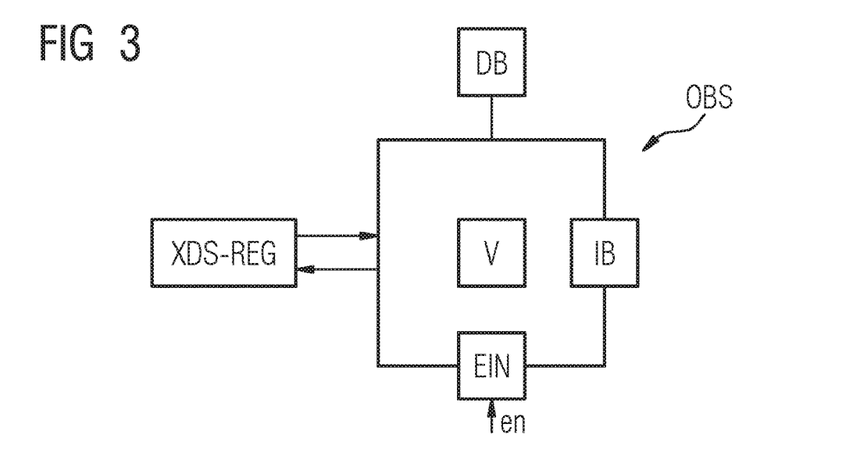
FIG. 3 shows a block diagram of a node that implements a central broker service according to one example embodiment of the invention.

In FIG. 3 is a schematic depiction of the architecture of the Broker node OBS on which the central broker service is implemented. It includes a broker-extraction interface EIN to receive the extraction message en and a further interface for communication with the registry XDS-REG and a further broker-input interface IB, which is used to receive the request an from the client CL. A processing unit V is used to resolve the received request an and to determine a client identifier and to ascertain the parameters of the requested overview message uen for the patient. Preferably, a patient ID is also transmitted in the request an and detached on the broker service node OBS.

Figure 4:
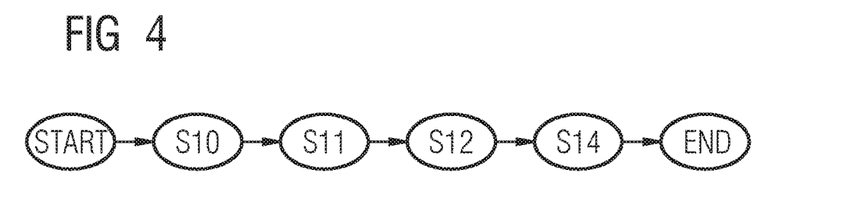
FIG. 4 shows a flow diagram of a method for execution on an extraction node.

The following describes with reference to FIG. 4 a course of the method executed on the extraction node OES.

After the start of the method, in step S10 the data record ds is received from the source XDS-S and in step S11 preconfigured parameters with their values are selected. Here, for example, relevant parameters are selected (for example weight, age, allergy, anesthetic gas composition) and their values determined in order to generate an extraction message en therefrom in step S12. The extraction message en then, for example, contains the information <code for weight>, 75, <optional unit> kg, <document ID>, <patient ID>. The extracted information is sent in step S14 to the broker service, which stores the information, in particular in the database DB. Here, it is important to stress that the stored data is not the original, sensitive medical data, but only excerpts or non-safety critical extracts thereof. The data collection formed can then advantageously be used for the implementation of certain operations (such as, for example, the automatic creation of an overview message or a patient summary or even requests for specific values and/or further (for example statistical) evaluations of the data). The method can be operated in PUSH operation so that newly generated documents or data records are always shifted to the extraction node. Alternatively, the generated data records ds can also be supplied to the extraction service at specific times or following configurable events. Alternatively, the method is operated in PULL mode so that the extraction node triggers and requests the sending of data records ds.

Figure 5:
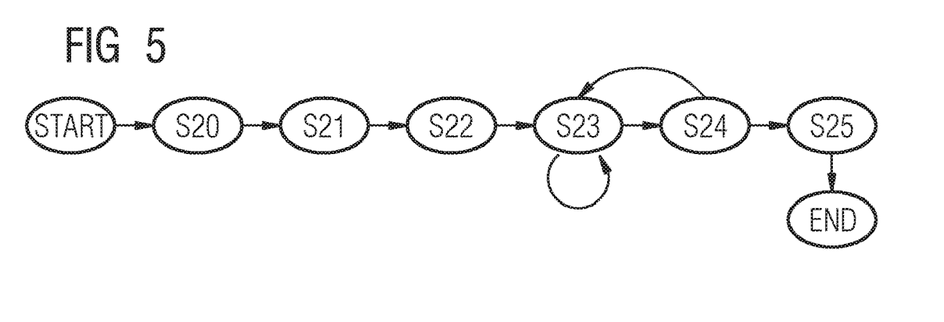
FIG. 5 shows a flow diagram of a method for execution on a broker node.

The following describes with reference to FIG. 5 a course of the method executed on the broker node OBS.

After the start of the method, in step S20 the request an is received from the client CL. This is resolved in step S21 in order to determine the client identifier and to ascertain the desired parameters of the request or the requested overview message uen. Then, in step S22, the connected database DB can be accessed in order to search for and aggregate the extraction messages en that correspond to the ascertained parameters. Herein, therefore, preferably all extraction messages en including the parameters are ascertained. As an interim result, a list with ascertained extraction messages en is generated. Each extraction message en typically includes several parameters. Therefore, this is only an interim result since it is still necessary to check for each of the parameters whether the requesting client CL is also authorized by virtue of role and request context to access the documents from which the respective parameter was extracted. A parameter can also be contained in several documents or data records ds. It is evident to the person skilled in the art that this task is associated with a high computing load. The role and the request context are acquired on the generation of the request by the client CL and sent in a data packet with the request query in the request message an to the broker service.

One important advantage of the solution according to at least one embodiment of the invention can be seen in the fact that these computing-intensive operations can be completely outsourced to the cloud, i.e. to the central broker service or the broker node OBS, and do not have to be executed at the local nodes or the client CL. In particular, there is no need for database access and or to perform a search on the local nodes and this makes the procedure suggested here very efficient.

In step S23—once again proceeding from the broker service—the central registry XDS-REG is accessed in order, on the basis of the client identifier determined, to check an existing authorization for the client CL to access the respective document/data record ds containing the respective parameter of all aggregated extraction messages en. In the case of affirmation (i.e. authorization exists), in step S24 the respective parameter is inserted in the overview message uen. These steps are repeated iteratively for all authorizations for all data records ds for all parameters of all extraction messages en in the interim result until it has been clarified for all elements whether access authorization exists or not. It is then ultimately possible to create the overview message uen in step S25. It can be supplied via a standardized transaction to the client CL. The method can end after this.

Figure 6:
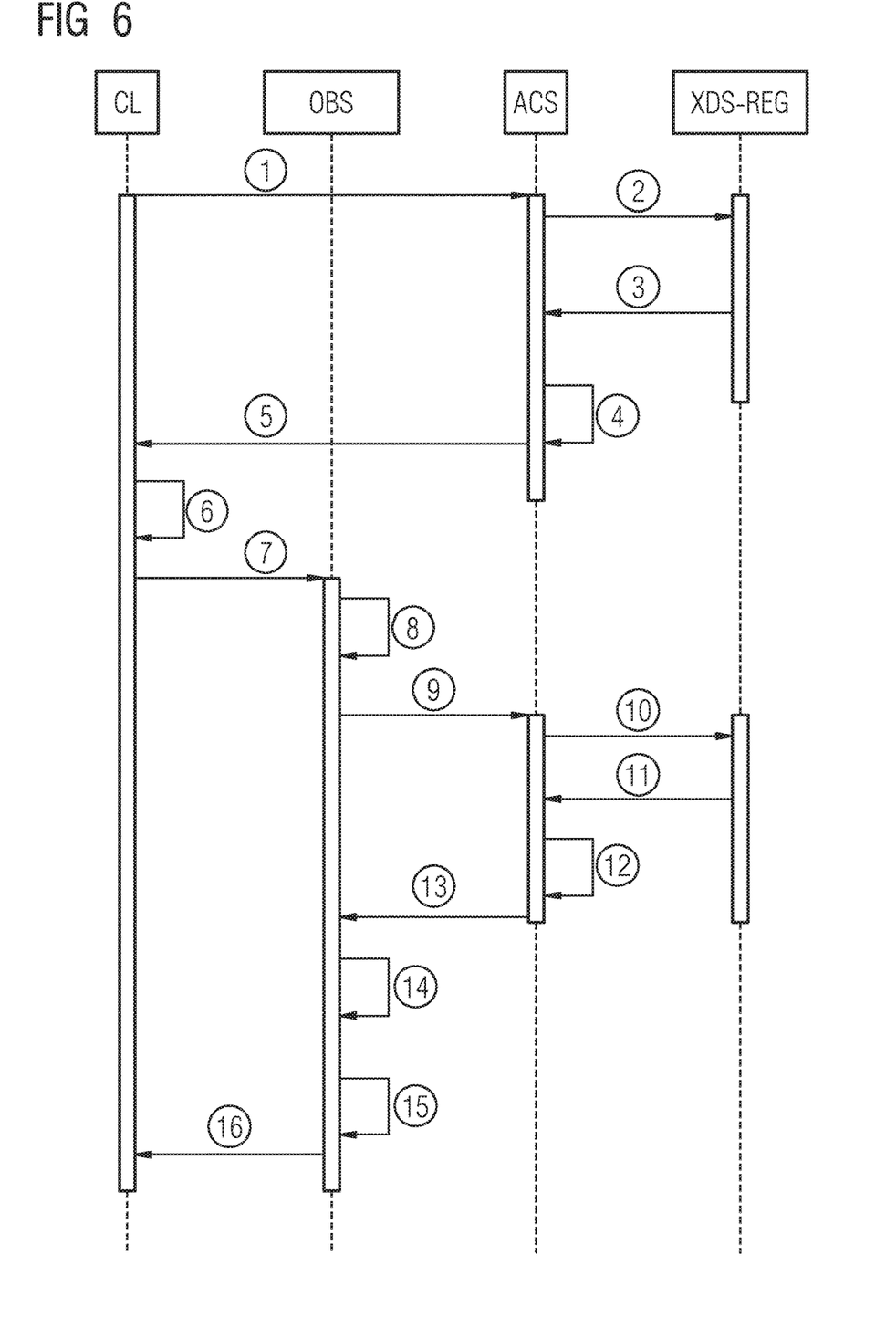
FIG. 6 shows a sequence diagram for message exchange between participating nodes.

FIG. 6 is a UML diagram showing data exchange between participating nodes according to a preferred implementation. Herein, an access control node is also provided on which an access control system ACS is implemented. Therefore, in the following, it will be referred to as an as ACS node for short and given the reference ACS. In alternative embodiments of the invention, the functions of the ACS node are integrated in another central node, in particular in the central registry XDS-REG.

The client CL represented in FIG. 6 can be an XDS receiver (i.e. a data sink, for example a physician who wishes to request data) or a XDS transmitter (and hence a data source), that generates data itself. With transaction 1, the client CL can access the ACS node which then registers the data record ds with transactions 2, 3 in the XDS registry XDS-REG. The ACS node can then carry out filtering operations, for example in order to implement acquired policies and further authorizations. With transaction 5, a result can be output to the client C1.

With the transaction 7 represented in FIG. 6, the client CL issues a request an to the broker service, as shown in FIG. 6. When the broker service has detached the necessary data from the request an, it is able, with transaction 8, to perform a search—corresponding to the request an and the client CL—for extraction messages en in the database DB. Then, in transaction 9, the ACS-node is accessed (or the registry XDS-REG is accessed directly), which, with transaction 10, accesses the registry XDS-REG in order to ascertain the access authorizations and provide them at the ACS node with transaction 11. There, filter operations can be performed with transaction 12. It is also possible for a plurality of filter operations 12 to be performed one after the other in order, for example, to fulfill stored policies (which can, for example, regulate that certain documents/data records ds must not be issued to certain clients CL or only issued to them in predefined time periods). It can also be the case that the forwarding of certain data records ds is linked to the consent of the patient, that is set (or not set) as a flag in a register. Accordingly, filtering is performed for the data records for which consent has been given.

The use of further control and regulating mechanisms is also within the scope of embodiments of the invention. The filter operation performed by the ACS node may make it necessary to access further nodes (for example for data reconciliation). However, for reasons of better clarity, these further nodes are not shown in FIG. 6. With transaction 13, the interim result can be forwarded to the broker service This can carry out still further processes with the operation 14 and for example remove certain extraction messages en from the overview message uen for which there is no authorization. With transaction 15, the result with the overview message uen is assembled specifically for the requesting client CL and output to this client with transaction 16. The result is preferably a document in CDA format (Clinical Document Architecture of the HL7 standard).

The following shows an example for an overview message uen, wherein, however, the document identifier is not explicitly named, but has a similar structure to that of the patient identifier <Patient id>:

```json
{
    "resourceType":"Observation",
    "contained":[
        {
            "resourceType":"Patient",
            "id":"1",
            "identifier":[
                {
                    "use":"usual",
                    "system":"1.1.1",
                    "value":"ee499dd1-06f5-4335-9304-67536aa5c6ad"
                }
            ]
        }
    ],
    "status":"preliminary",
    "category":[
        {
            "coding":[
                {
                    "system":"http://hl7.org/fhir/observation-category",
                    "code":"vital-signs",
                    "display":"Vital Signs"
                }
            ]
        }
    ],
    "code":{
        "coding":[
            {
                "system":"http://loinc.org",
                "code":"3141-9",
                "display":"Weight Measured"
            }
        ],
        "text":"LOINC Body weight"
    },
    "subject":{
        "reference":"#1"
    },
    "effectivePeriod":{
        "start":"2017-02-01T13:33:17+01:00",
        "end":"2017-02-01T13:33:17+01:00"
    },
    "valueQuantity":{
        "value":80.0,
        "unit":"kg",
        "system":"http://unitsofmeasure.org",
        "code":"[kg]"
    },
    "comment":""
}
```

In summary, it can be established that the suggestion according to the method of an embodiment enables medical data records ds to be indexed in a configured way and in filed in indexed form in order to enable a very efficient search in the extensive data records on a dedicated high-capacity server in order to be able to generate an overview file or an overview message uen and, at the same time, both comply with safety regulations and follow existing standards without it being necessary to make changes to the existing management service or to the existing hardware.

A fundamental concept of at least one embodiment of the present invention resides in the provision of a system with which an overview message can be automatically created without having to make changes to the existing infrastructure of the medical IT system. The overview message uen can contain representations of preconfigured data evaluations, such as a patient summary or other evaluations, such as, for example, the issue of a warning signal in the event of critical changes to the data records. Skillful sequencing and concatenation of transactions enables the overview message uen to be calculated such that it only contains components for which the authorization system ACS, XDS-REG has validated access authorizations. One of the key points of the present application is that the information contained in the overview message uen, the so-called observations, are not only extracted and filed, but can also be processed with existing document-based authorization systems. This enables costs to be reduced since it is not necessary to finance new hardware. It is possible to use existing systems with usual standards.

This solution is able to achieve the technical advantage that all computing-intensive calculations can be shifted to the cloud. It is possible for a dedicated high-performance service node to be provided for this in the cloud. The generation process for the generation of the overview message can be performed completely at the data generation side and not at the data consumption side, i.e. not at the client side.

Finally, reference is made to the fact that the description of the invention and the example embodiments should in principle not be understood to be restrictive with respect to a specific physical implementation of the invention. All features explained and demonstrated in connection with individual embodiments of the invention can be provided in different combinations in the subject matter of the invention in order to implement their advantageous effects simultaneously.

For a person skilled in the art it is in particular evident that the invention can be used not only with IHE XDS-Systems but also with other standards. The local nodes are preferably separate from the central nodes. However, in special embodiments of the invention, for example, if the data generation side has numerous resources, it is also possible for the broker service to be implemented on the same node as the extraction service. However, typically the node OBS of the broker service and the node OES of the extraction service are implemented distributed between a plurality of physical products.

The scope of protection of embodiments of the present invention is defined by the following claims and is not restricted by the features explained in the description or shown in the figures.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for operating a central broker service for handling a request from a client for an overview message for a patient based on a standardized platform, the method comprising:

receiving the request at the central broker service for the overview message from the client;

resolving the request for the overview message received from the client, determining a client identifier of the client and ascertaining parameters of the overview message requested;

accessing a database containing patient data in the form of extraction messages, the extraction messages being electronic data records previously extracted from medical data acquired from read-in data records stored in a data source different from the database and not directly accessible by the central broker service, and aggregating one or more extraction messages containing only excerpts and/or non-safety critical extracts of the read-in data records corresponding to the parameters ascertained;

accessing a central registry that is separate from and remote to the database and, based upon the client identifier determined, checking for an existing authorization stored in the central registry for access rights of the client to access a respective document containing a respective parameter that the client has authorization to access, of the parameters ascertained, pertaining to all aggregated extraction messages; and executing, upon the check indicating existence of authorization, at least:

generating the overview message, containing a summary of patient specific parameters and a link to more detailed information in the read-in data records from which the extraction messages are drawn, on a graphic user interface without having the acquired medical data or the data source different from the database accessible to the central broker service, the generating including inserting of the respective parameter in the overview message.

2. The method of claim 1, wherein the overview message is generated dynamically and only when required at least one of upon request of the client and during access to the database.

3. The method of claim 1, wherein the overview message is supplied as a fully structured document.

4. The method of claim 1, wherein an authorization for the client is based on an authorization rule, wherein the authorization rule is held in the central registry, and wherein the authorization rule is changeable during execution of the method.

5. The method of claim 1, wherein the generating of the overview message includes taking at least one of the authorization of the client to access data records and contextual parameters of the request received, into account.

6. The method of claim 5, wherein, the generating of the overview message includes filtering the contextual parameters of the request received in accordance with configurable filter criteria.

7. The method of claim 6, wherein the overview message includes a link to the respective document in accordance with the contextual parameters of the request received.

8. The method of claim 1, wherein the overview message is not stored in the registry.

9. The method of claim 1, wherein all calculations for the generating of the overview message are executed in full by the central broker service on a central broker node.

10. The method of claim 1, wherein the standardized platform is an Integrating the Healthcare Enterprise (IHE) Cross-Enterprise Document Sharing (XDS) platform, and wherein the data source not accessed by the broker service is an XDS repository, and the central registry is a registry according to the XDS standard.

11. A central broker node usable to execute a broker service for handling a request from a client for an overview message for a patient based on a standardized platform, the central broker node comprising:

memory storing computer-readable instructions; and one or more processors configured to execute the computer-readable instructions such that the one or more processors are configured to perform operations including, receiving, at the central broker node, the request for the overview message from the client;

reading in an extraction message, the extraction message being an electronic data record previously extracted from medical data acquired from read-in data records stored in a data source not directly accessible by the central broker node;

resolving the request received, to determine a client identifier, and ascertaining parameters of the overview message requested;

accessing a database different from the data source and aggregating extraction messages containing only excerpts and/or non-safety critical extracts of the read-in data records corresponding to the parameters ascertained;

accessing a central registry, that is separate from and remote to the database, and, based upon the client identifier determined, checking an existing authorization stored in the central registry for access rights of the client to access a respective document containing a respective parameter that the client has authorization to access, of the parameters ascertained, pertaining to all aggregated extraction messages;

inserting, upon the check indicating existence of authorization, the respective parameter in the overview message; and generating the overview message, containing a summary of patient specific parameters and a link to more detailed information in the read-in data records from which the extraction messages are drawn, on a graphic user interface without having the acquired medical data or the data source different from the database accessible to the broker service.

12. A system for generating an overview message for a patient based on a standardized platform and for operating a central broker service and an extraction service, the system comprising:

a first processor configured
- to read in a data record from a local data source;
- to select parameters of the data record, read-in, and to generate an extraction message;
- to send the extraction message, once generated, to a database of a central broker service;

a local repository not directly accessible by the central broker service for local storage of the data records, including the data record read-in, and for sending metadata of the data records, including a link to the data records, to a central registry, that is separate from and remote to the database of the central broker service containing patient data;

a second processor configured
- to receive a request from a client for the overview message;
- to be in data exchange with the first processor, to read in an extraction message;
- to resolve the request for the overview message received from the client, to determine a client identifier, and to ascertain parameters of the overview message requested,
- to access the database of the central broker service to aggregate extraction messages containing only excerpts and/or non-safety critical extracts of the read-in data records corresponding to the parameters ascertained,
- to access the central registry to, based upon the client identifier determined, check for an existing authorization stored in the central registry for access rights of the client to access a respective document containing a respective parameter that the client has authorization to access, of the parameters ascertained, pertaining to all aggregated extraction messages, and
- upon the check indicating existence of authorization, to insert the respective parameter in the overview message and to generate the overview message on a graphic user interface without having acquired medical data or the data source different from the database accessible to the central broker service, the overview message containing a summary of patient specific parameters and a link to more detailed information in the read-in data records from which the extraction messages are drawn.

13. The method of claim 1, wherein the overview message is supplied as a fully structured document, formatted in accordance with a Clinical Document Architecture (CDA) standard.

14. The method of claim 1, wherein, the generating of the overview message includes filtering parameters of the request received in accordance with configurable filter criteria.

15. The method of claim 1, wherein the overview message includes a link to the respective document containing at least one parameter of the request received.

16. The method of claim 8, wherein the overview message is not on a node but is only made available to the client.

17. A non-transitory computer readable medium storing computer program code for executing the method of claim 1 when the computer program code is executed on a computer.

* * * * *